(12) United States Patent
Srinivasan et al.

(10) Patent No.: US 6,796,187 B2
(45) Date of Patent: Sep. 28, 2004

(54) WIRELESS MULTI-FUNCTIONAL SENSOR PLATFORM, SYSTEM CONTAINING SAME AND METHOD FOR ITS USE

(75) Inventors: Regaswamy Srinivasan, Ellicott City, MD (US); Robert Osiander, Ellicott City, MD (US); Jane W. Spicer, Columbia, MD (US); Francis B. Weiskopf, Jr., Catonsville, MD (US); Kenneth R. Grossman, Olney, MD (US); Russell P. Cain, Columbia, MD (US); Bliss G. Carkhuff, Laurel, MD (US)

(73) Assignee: The Johns Hopkins University, Baltimore, MD (US)

( * ) Notice: Subject to any disclaimer, the term of this patent is extended or adjusted under 35 U.S.C. 154(b) by 127 days.

(21) Appl. No.: 10/220,102

(22) PCT Filed: Dec. 7, 2001

(86) PCT No.: PCT/US01/46806

§ 371 (c)(1),
(2), (4) Date: Aug. 27, 2002

(87) PCT Pub. No.: WO02/46701

PCT Pub. Date: Jun. 13, 2002

(65) Prior Publication Data

US 2004/0004554 A1 Jan. 8, 2004

Related U.S. Application Data

(60) Provisional application No. 60/254,118, filed on Dec. 8, 2000, and provisional application No. 60/284,018, filed on Apr. 16, 2001.

(51) Int. Cl.[7] .................................................. G01B 5/00
(52) U.S. Cl. ........................................................ 73/784
(58) Field of Search ........................ 73/784, 801, 802, 73/803, 805, 804, 811, 778, 786

(56) References Cited

U.S. PATENT DOCUMENTS

| 4,147,596 A | 4/1979 | Baboian et al. |
| 4,703,253 A | 10/1987 | Strommen |

(List continued on next page.)

FOREIGN PATENT DOCUMENTS

| DE | 3736873 | 5/1989 |
| GB | 2342998 | 4/2000 |
| JP | 07306299 | 11/1995 |
| WO | WO 00/50849 | 8/2000 |

OTHER PUBLICATIONS

PCT International Search Report PCT/US01/46806 Dated Jul. 12, 2001.
Embedding Sensor for Corrosion Measurement, SPIE Proceedings, vol. 3587, Non Destructive Evaluation of Bridges & Hgwys.III, p 16–27 by Kelly et al.
Embeddable Microinstruments for Corrosion Monitoring Paper 97294, Corrosion 97, Natl. Assn. of Corr. Eng., (NACE) 1997, By Kelly et al.

*Primary Examiner*—Max Noori
(74) *Attorney, Agent, or Firm*—Albert J. Fasulo, II

(57) ABSTRACT

A multi-functional sensor system for simultaneously monitoring various parameters such as the structural, chemical and environmental conditions associated with a medium to be monitored, e.g., bridges, high-rise buildings, pollution zones, is provided wherein the system includes at least a plurality of wireless multi-functional sensor platforms embedded in the medium in which an interrogation unit transmits power and receives responses. Each wireless multi-functional sensor platform includes multiple channels for accommodating a plurality of sensor types to simultaneously monitor the parameters associated with the medium. Thus, the wireless sensor platforms are formed to include those sensor types which are considered germane to the intended medium to be monitored.

16 Claims, 8 Drawing Sheets

U.S. PATENT DOCUMENTS

| | | |
|---|---|---|
| 4,844,076 A | 7/1989 | Lesho et al. |
| 5,015,355 A | 5/1991 | Schiessl |
| 5,446,369 A | 8/1995 | Byrne et al. |
| 5,650,725 A | 7/1997 | Powell et al. |
| 5,700,090 A * | 12/1997 | Eryurek .................. 374/210 |
| 5,785,842 A | 7/1998 | Speck |
| 5,792,337 A | 8/1998 | Padovani et al. |
| 5,895,843 A | 4/1999 | Taylor et al. |
| 5,971,597 A * | 10/1999 | Baldwin et al. ............ 700/277 |
| 5,982,297 A * | 11/1999 | Welle .................... 340/870.16 |
| 6,034,296 A | 3/2000 | Elvin et al. |
| 6,088,585 A * | 7/2000 | Schmitt et al. ............. 455/411 |
| 6,535,116 B1 * | 3/2003 | Zhou ......................... 340/447 |

\* cited by examiner

WIRELESS MULTI-FUNCTIONAL SENSOR PLATFORM, SYSTEM CONTAINING SAME AND METHOD FOR ITS USE

CROSS-REFERENCE TO RELATED APPLICATIONS

This application claims the benefit of prior filed, co-pending U.S. provisional application serial Nos. 60/254,118, filed on Dec. 8, 2000 and 60/284,018, filed on Apr. 16, 2001.

BACKGROUND OF THE INVENTION

1. Field of the Invention

The present disclosure generally relates to a wireless multi-functional sensor platform, a sensor system containing same and method for its use. More particularly, the present disclosure is directed to an in-situ multi-functional sensor system containing a plurality of wireless multi-functional sensor platforms and method for providing long-term monitoring of various parameters associated with a medium, e.g., concrete, by embedding the sensor system within the medium to predict the onset of degradation and thus aid in the scheduling of maintenance, management and repair thereof.

2. Description of the Related Art

In the United States, billions of dollars have been spent in the construction of highways, freeways and their associated overpasses, bridges and buildings. One of the most important problems facing the nation is determining how to maintain the integrity of this system of roads and other structures at an acceptable cost. Obviously, it would be advantageous for practitioners in the art to have the benefit of a permanent, early-warning system for detecting structural degradation in the earliest stages.

One of the primary applications of this technology is in the area of bridge-deck monitoring. Currently, bridge deck monitoring is based on individual sensor measurements or periodic visual inspection by trained personnel. This approach doesn't detect bridge deck or foundation degradation until it has already reached an advanced state. By this time, remedial actions are more expensive than if the problem had been detected earlier. In addition, significant degradation impacts repair schedules and quality of service for the bridge.

Yet another problem associated with present day sensor systems for use in bridge monitoring is that the sensors are not distributed throughout the bridge deck. Instead, they are used only for discrete measurements, mostly due to economic limitations. Furthermore, the cost of making measurements employing present day technology is high due to installation and monitoring requirements.

Further problems associated with prior art solutions for bridge monitoring is that recent research has focused on mechanical sensing such as stress/strain and pressure. Sensors that are being designed to address corrosion-related degradation are limited to specific parameters such as, for example, chloride and temperature, or gross measurements of physical properties such as conductivity.

Thus, it would be particularly advantageous to employ sensors which measure a multitude of parameters for various mediums that extend beyond those described above. Such parameters may include those related to the structural, chemical and/or environmental conditions associated with a medium such as, for example, magnetism, noise, pH, pressure, shock, strain, stress and vibration. Accordingly, a need exists for a multi-functional sensor system for providing long-term monitoring of a plurality of parameters of a medium to preemptively detect the onset and degree of degradation. In this manner, protective measures can be promptly taken to ensure that the medium is properly maintained.

SUMMARY OF THE INVENTION

It is an object of the present invention to provide an early-warning multi-functional sensor system for monitoring a plurality of parameters, e.g., structural, chemical and/or environmental conditions, associated with a medium such that the onset of degradation can be detected employing the multi-functional sensor system.

It is a further object of the present invention to provide an early-warning multi-functional sensor system that may be embedded in a medium such as, for example, concrete buildings, bridges or in contaminated ground zones, for long-term monitoring of the medium to both detect the onset of degradation and to prevent or forestall further degradation.

Yet another object of the present invention is to provide a plurality of wireless multi-functional sensor platforms for use in the early-warning sensor system that are compact in size, relatively low in cost and are capable of being remotely powered to facilitate their long term use such that numerous sensors may be used in a single project, e.g., embedded in a reinforced concrete bridge. The sensor platforms are designed to be powered and queried remotely as often as required for use in measuring a plurality of parameters of the medium in which they are embedded.

A further object of the present invention is to provide a plurality of wireless multi-functional sensor platforms that are capable of monitoring the medium in a nondestructive manner.

It is a further object of the present invention to provide a plurality of wireless multi-functional sensor platforms which may serve as an attachment base for supporting a plurality of sensor types on each platform specifically selected for use in monitoring a particular parameter associated with the medium to which the sensor platforms are embedded in.

It is yet a further object of the present invention to provide a plurality of wireless multi-functional sensor platforms that exhibit extremely high reliability for a prolonged period, e.g., on the order of several decades.

In keeping with these and other objects of the present invention, an early-warning multi-functional sensor system and method for using same are provided which includes a network of cost-effective, embeddable, remotely powered, ultra-small, ruggedized and long-lasting wireless multi-functional sensor platforms that are impervious to harsh environmental conditions such as salt, mechanical and thermal stress. The sensor platforms are particularly suited for long-term field measurements of parameters in a harsh environment. The sensor platforms are preferably constructed from a housing material that is of low cost and requires only standard automated machining, e.g., a ceramic material.

Accordingly, the sensor platforms are multi-functional in that they serve as platforms for attaching a multitude of sensor types (e.g., temperature, conductivity, pressure, pH, etc.) thereto for monitoring various parameters specific to the medium to be monitored. This capability of interchanging sensor types dependent upon the particular medium makes the sensor system of the present invention suitable for use in a wide variety of monitoring situations. Thus, when the platforms are employed in the sensor system, sensor platforms having a plurality of sensor types attached thereto are distributed throughout the medium to be monitored to acquire data directed to, for example, structural, chemical and environmental data, associated with the medium. The sensor system therefore advantageously provides an early warning indication of the present state of the monitored medium to aid in the medium's timely maintenance and/or repair.

According to one aspect of the present invention, the operation of the sensor system includes disposing a plurality or network of wireless multi-functional-sensor platforms throughout a medium or zone in the medium to be monitored, with each of the sensors generating an output. Sensor data can then be collected periodically, via wireless means, which may be combined with historical data for analysis to ascertain the health of the medium.

Data collection is performed by an interrogation unit operable to generate power to and receive responses from the plurality of sensor platforms. In this regard, the data is collected in a non-invasive manner without impact on the medium being monitored.

In one exemplary application, the system of the invention involves distributing the wireless multi-functional sensor platforms approximately every two meters throughout a medium during or after construction. Periodically, a field data acquisition system passes over the network of sensors to infer the sub-surface environment. The resulting data is then used to forecast potential problem regions within the medium and measure the evolution of the structural, chemical and environmental parameters of the medium over time. As such, the sensor system provides an early warning indication of potential and ongoing adverse structural, chemical and environmental changes within the medium.

Other objects and advantages of the present invention will become more fully apparent from the following, more detailed description and the appended drawings, which illustrate several embodiments of the invention.

DETAILED DESCRIPTION OF THE PREFERRED EMBODIMENTS

Figure 1:
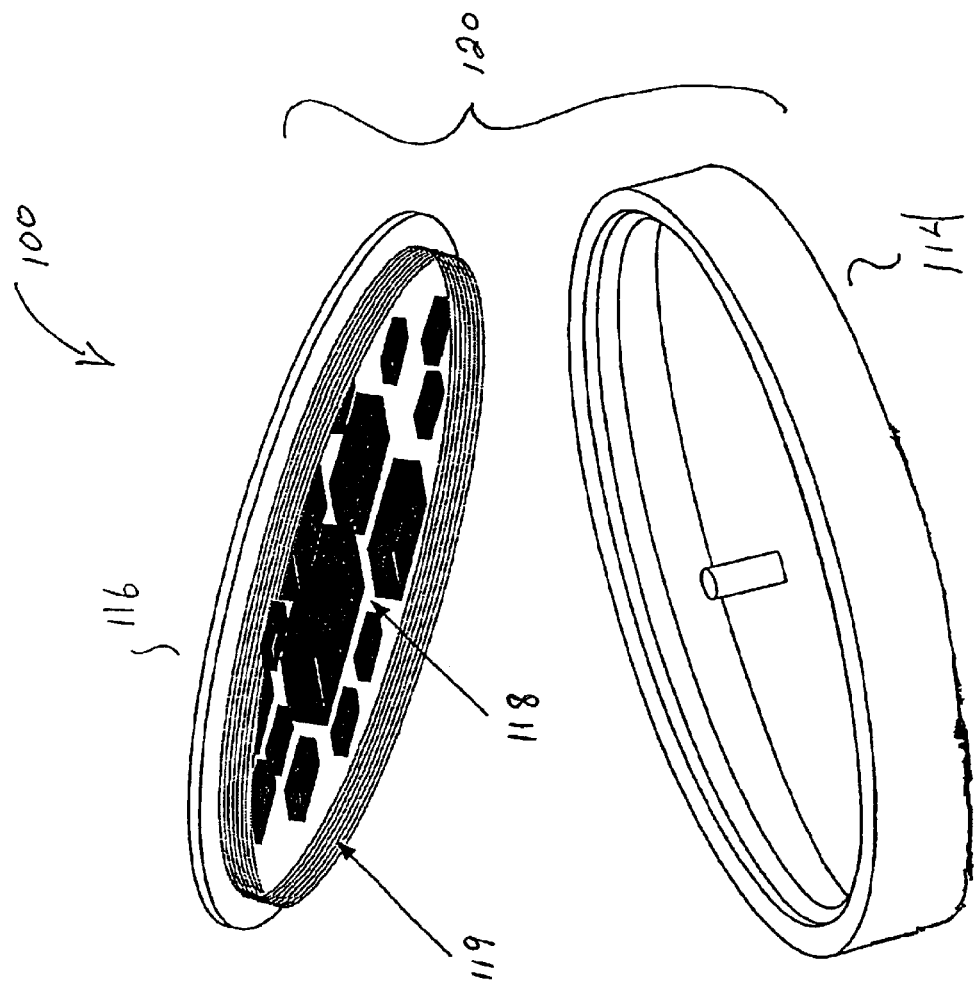
FIG. 1 illustrates an exploded view of a wireless embedded sensor platform, according to the present invention.

The sensor system of the present invention provides a long-term monitoring capability of a harsh environment for various mediums in need of monitoring. Such mediums include, but are not limited to, asphalt, composites, plastics, cement, concrete, e.g., structures such as buildings or bridges, apparatuses, e.g., heavy machinery, and zones of interest, e.g., stream run-off, pollution or contamination zones around areas such as, for example, storage tanks, pipelines, bays and streams. In addition to the foregoing mediums, the present invention will find general applicability to any medium in which long-term monitoring of a harsh environment is a requirement. For optimum results, however, the medium should be relatively non-absorptive of the electromagnetic energy spectrum used to interrogate the wireless embedded sensor platforms.

Accordingly, by employing the sensor system disclosed herein, relevant parameters such as the aforementioned structural, chemical and environmental conditions associated with the medium can be monitored over an extended period of time, on the order of several decades, to assess the state of health of the medium in order to predict the onset or occurrence of degradation. Thus, the present invention provides an early detection or warning capability of such degradation in order to schedule corrective measures such as, for example, maintenance and repair, in a timely manner rather than having to incur more costly and time-consuming repair at a later stage of degradation.

For example, in the case of a structure such as a bridge, the system of the present invention allows authorities to routinely perform an accurate and relevant assessment of structural integrity to schedule maintenance and repair operations in a timely and more cost effective manner. As a further example, in the case of a pollution zone, the present invention provides authorities with a capability for monitoring the extent and rate of the pollution zone to prevent further degradation and to assess the effects of remediation processes.

The sensor system of the present invention includes at least a plurality of ultra-small, rugged, wireless sensor platforms that are embedded in the medium to be monitored by strategically or randomly placing the platforms throughout the medium. The wireless sensor platforms are multi-functional in that they provide a support base for the insertion of a multitude of sensor types (e.g., pressure, conductivity, pH, stress, strain, etc.), which are described hereinbelow, for measuring parameters of relevance to an intended monitored medium. For example, in the case where stress, temperature and pH are considered relevant parameters for a particular monitored medium, then a stress sensor, a strain sensor and a pH sensor will be implemented in the sensor platform having three sensor channels for accommodating the three selected sensors at the configuration stage. It is well within the scope of the invention to construct a sensor platform that contains a greater number of sensor channels for accommodating additional sensor types.

A particular embodiment for the sensor system of the present invention is that for sensing a change in the sub-surface environment in bridges. The Federal Highway Administration has identified over 170,000 US bridges in need of some substantial repair, many of which were due to deck rebar corrosion. One of the problems associated with such structures as bridges, high-rise parking lots and large buildings has been the absence of precise and quantifiable information regarding the corrosion state of the rebars and the corresponding need for counter-corrosion measures. The sensor system of the present invention provides a capability for non-invasively monitoring the evolution of degradation over time without impacting the monitored medium.

In addition to collecting relevant structural, chemical and environmental data, the sensor system of the present invention can advantageously collect supplemental data which results from the interaction between the plurality of individual wireless embedded sensor platforms. As one example, acoustic measurements may be suitable for the detection of cracks in concrete. However, acoustic measurements are somewhat limited due to the poor propagation of acoustic waves in heterogeneous materials such as concrete. But as the distance between sender and receiver is reduced, as in the case of transmission between two embedded and proximally located sensor platforms, such a measurement becomes feasible.

In a preferred embodiment, data specific to the structural, chemical and environmental conditions associated with the medium is collected periodically from a network of wireless embedded sensor platforms by wirelessly interrogating the wireless platforms using, for example, a field data acquisition system, which periodically passes over the platforms to infer the sub-surface environment of the medium. The resulting data can then be combined with historical data, obtained from prior interrogations, to forecast potential problem regions within the medium to enable prediction of expected failures and to make necessary repairs in a timely manner.

The present invention also provides a safety factor as well as an economic factor, and has application for degradation monitoring for transportation safety relative to bridges, tunnels, underpasses, overpasses, etc. Also, the invention has applications for environmental monitoring, such as acid rain conditions and its effect on degradation of structural materials, or other industrially or urban-induced problems. Thus, the invention is also an in-situ sensor system, employing a plurality of wireless embedded sensor platforms to provide information regarding environmental conditions.

Since the rates/modes of structural degradation on a given structure are related to environmental conditions, such as low or high pH, stress, temperature and vibration, the sensor system of the present invention is well-suited as an "early warning" system to flag the onset of electrical, chemical and structural degradation. Thus, the network of wireless embedded sensor platforms which simultaneously monitor the above and other parameters provide both maintenance and safety information.

Although specific reference is made herein to embedded sensors, those skilled in the art will readily appreciate that the term "embedded" as used herein is intended to be interpreted in its broadest sense to include, for example, sensors disposed on a surface of or integrated with a medium. Further, it is to be understood that the sensors may be distributed in any manner throughout a medium so as to optimize the information provided therefrom. By way of example, in the case of a concrete pylon, it may be desirable to distribute the sensors with different densities on the top and bottom of the concrete pylon where stresses may be higher on the top of the pylon. In other applications, cost may be a driving factor in the determination of the distribution and densities of the sensors.

When embedding the wireless sensor platforms in the medium, the platforms can be held in place by structural members such as, for example, reinforcements or rebars using a holder or attached either mechanically or via a bonding material to said structural members. They can also be placed at a layer boundary in layered structures. Likewise, they can be inserted into the structure during or after construction. The devices could also be epoxied to the back of sheetrock during construction to monitor moisture or temperature of the inner wall of the medium.

Wireless Embedded Sensor Platforms

The sensor system of the present invention employs a plurality of wireless embedded sensor platforms strategically or randomly distributed throughout a medium to be monitored. Each sensor platform is capable of supporting a plurality of sensor types for measuring a wide variety of structural, chemical and environmental conditions associated with the monitored medium. The sensor types capable of support by the platform include, but are not limited to, temperature, conductivity, pH, magnetism, noise, pressure, shock, strain, stress, vibration, etc. Other sensor types not explicitly recited herein may be used in conjunction with the sensor platform of the present invention.

Representative of the sensor types used herein are discussed in Appendix A which is attached hereto. Each of the sensor types discussed in Appendix A share the common characteristics of being small, inexpensive, requiring very little power, and are easily integrated with the sensor platform. Appendix A describes the operating principle of each sensor and the physical variables they monitor.

The following is an overview of the mechanical and electrical features of the wireless embedded sensor platforms employed in the sensor system of the present invention.

Mechanical Overview

Referring now to FIG. 1, wireless multi-functional sensor platform 100 of the present invention includes at least housing 120 and sensor electronics 118 enclosed within housing 120, which is discussed hereinbelow. In general, housing 120 will be formed from conventional materials known in the art. Preferred materials for use herein include, but are not limited to, ceramic materials such as alumina or macor and the like. As one skilled in the art would readily appreciate, dimensions and configurations for housing 120 can vary accordingly and can be determined on a case-by-case basis. For example, when housing 120 is disc-like in shape, housing 120 can be 1" in diameter. It is within the contemplation of the present invention to further reduce the size of housing 120 in future embodiments to a package volume less than 2.5 cm$^3$ (0.15 in$^3$).

In general, sensor housing 120 can include base 114 and cap 116. Base 114 can be constructed in a two-step process wherein a first step defines a conventional machining process to acquire the shape of the base such as the generally disc-like shape as depicted in FIG. 1. The second step involves defining a firing cycle to enable base 114 to reach a high mechanical strength. Subsequent to the second or firing cycle step, the housing material is substantially identical to production ceramic cast material.

Figure 2:
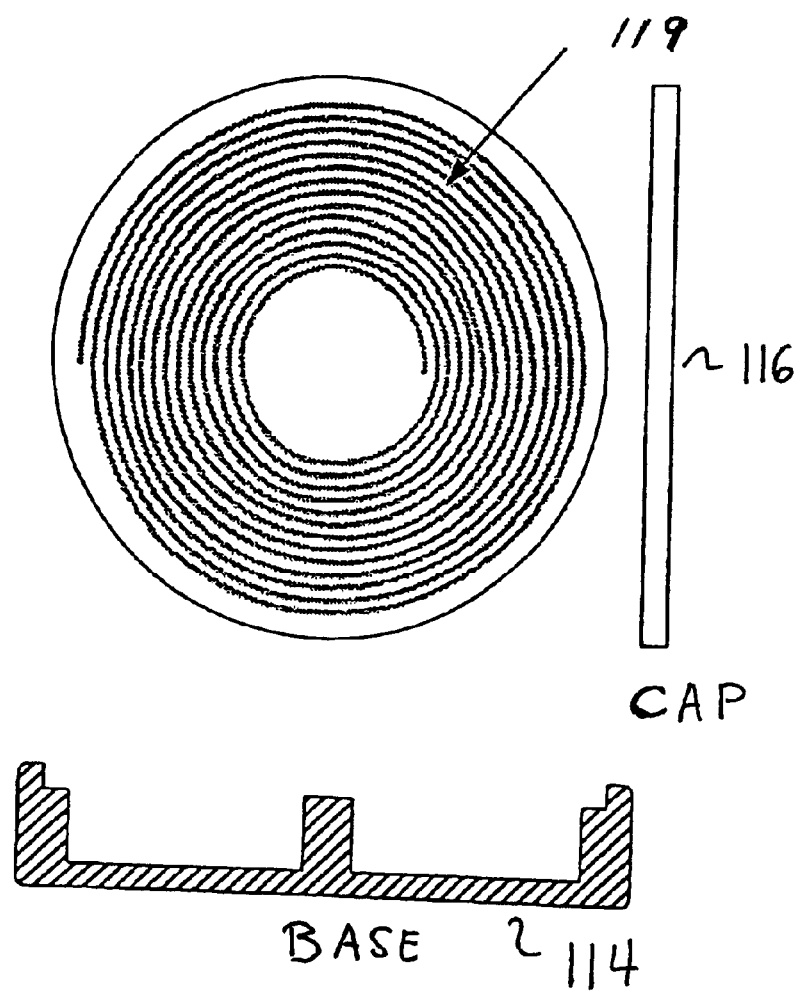
FIG. 2 illustrates a top view of the embedded patterned transmission antenna 119, constructed as a layer of the ceramic cap of the sensor platform of FIG. 1.

Cap 116 is generally a shape similar to that of base 114 such as a circular shaped low temperature co-fired ceramic (LTCC) cap 116 as depicted in FIG. 1. The cap 116 is preferably epoxy-mounted into the ceramic base 114. However, it is to be understood that other conventional means for mounting base 114 into cap 116 known to one skilled in the art can be used herein. In one embodiment, the cap portion 116 is constructed as comprising several layers 119. The layers can be of varying or the same thickness, e.g., a thickness for each layer ranging from about 0.001" to about 0.10" with an approximate thickness of 0.005" being preferred for each layer for structural integrity such that the an approximate final thickness of about 0.040" is achieved. One of the layers of the ceramic cap 116 is designed to function as a patterned transmission antenna. FIG. 2 illustrates a top view of the patterned transmission antenna constructed as a layer amongst several layers 119. Other layers (not shown) that can be included in layers 119 are a spacer layer, routing layers, power pickup coil layer as are within the purview of one skilled in the art.

In a preferred embodiment, the housing 120 is made from a machinable green bisque ceramic of 96% alumina. The green bisque material was selected as a preferred material based on meeting the requirements of low cost; requiring only standard automated machining and; having physical properties which are closest to a low temperature co-fired ceramic (LTCC) cap 116 which serves as a substrate upon which the sensor electronics 118 and patterned antenna 119 are assembled for attachment to base 114. The base 114 can be made from any type of inexpensive ceramic that is capable of being machined or cast. However, base 114 can also be milled directly from machinable ceramic, such as Macor, depending upon the suitability of the intended application.

As stated above, LTCC cap 116 serves as an assembly platform for the sensor electronics 118 which comprise a number of IC components attached to LTCC cap 116 using commercial IC packaging and assembly techniques and materials. In particular, the sensor electronics 118 are attached to LTCC cap 116 with, for example, gold vias and plating. Once assembled, LTCC cap 116 including the sensor electronics 118 is attached to the base 114 of sensor housing 120. LTCC cap 116 is preferably bonded to the base 114 with ceramic epoxies.

LTCC cap 116 can be a combination of tape dielectric materials with screen printed thick-film conductor. For example, the tape can be cut to the desired geometry; vias are mechanically formed where needed, and conductors are printed on the tape sheets. The various layers are then stacked and laminated into a monolithic structure which is dried and fired to produce the desired functional part. This produces a ceramic laminate, similar to a printed circuit board, with interlayers of conductor.

Figure 3:
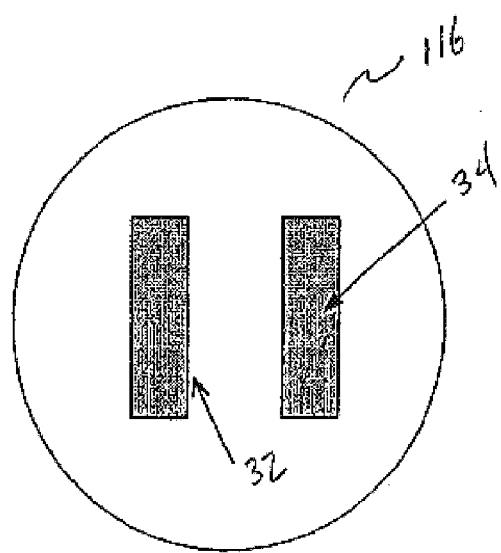
FIG. 3 illustrates a back or external view of the ceramic cap of the sensor platform of FIG. 1.

FIG. 3 shows a back view of the cap 116 for an application including a conductivity sensor. In the case where a conductivity sensor is used, two electrodes 32 and 34 collectively comprise a single conductivity sensor for making conductivity measurements. As shown, electrodes 32 and 34 physically protrude through the exterior or back portion of the cap 116 thereby coming into physical contact with the medium being monitored or measured (e.g., concrete). The conductivity sensor operates by driving a current out of one electrode 32 and allowing the current to flow through the medium to be returned to the other electrode 34. A potential is thus developed by virtue of the current flow. Inside the sensor platform 100, the potential that develops across the electrodes is measured, which is a measure of the resisitivity of the medium. Electrodes 32 and 34 are spaced and sized so that the measured potential can be transformed directly into a resistance measurement. Electrodes 32 and 34 may be constructed of palladium platinum. It is noted that not all sensors are required to be exposed to the harsh environment, and as such are wholly contained within the sensor housing 120.

Electronics Overview

Figure 4A:
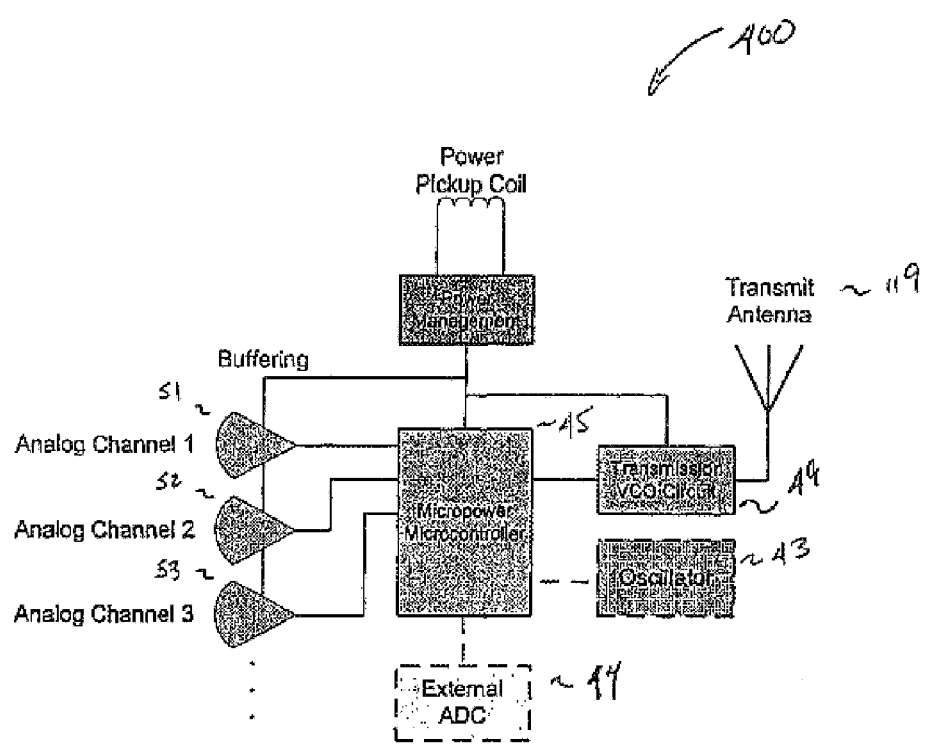
FIG. 4a illustrates a first embodiment of sensor electronics/circuitry contained within the sensor platform of FIG. 1.
Figure 4B:
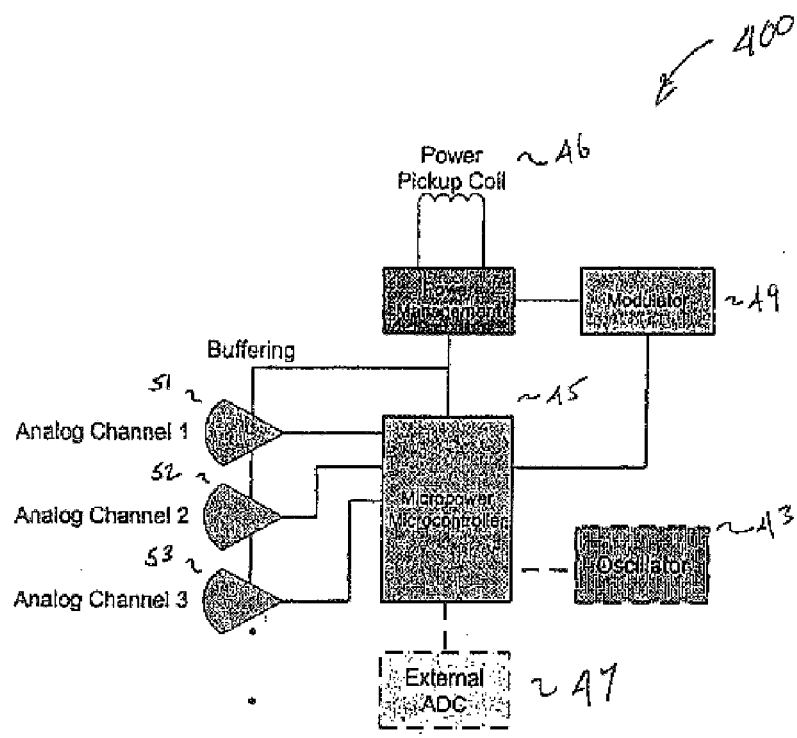
FIG. 4b illustrates a second embodiment of sensor electronics/circuitry contained within the sensor platform of FIG. 1.

Two embodiments of the sensor electronics/circuitry are illustrated in FIGS. 4a and 4b. In each embodiment, a micro-power processor 45 and associated circuitry provide the system control for a plurality of sensors types. A unique advantage of the present invention is that a plurality of sensors types may be attached to the sensor platform 100 to simultaneously monitor the desired parameters associated with the condition of the monitored medium. Further, each sensor platform 100 has a unique identification number that is recorded during installation for correlating obtained data to specific location within the monitored medium. In each embodiment, power is remotely provided to the sensor platform 100 using a method of near field induction while data is transmitted from the sensor platform 100 to a field acquisition unit via a radio frequency (RF) link in a first embodiment, or by means of absorption modulation, in a second embodiment. Each embodiment is further described below.

In FIGS. 4a and 4b three sensors 51, 52, 53 are shown. The sensors 51–53 perform the sensing function when power is provided from an interrogation unit via near field induction. Each sensor 51–53 provides as output, an analog signal to a dedicated channel of microprocessor 45. The microprocessor 45 may be a microprocessor, microcontroller, programmable array logic, gate array logic, or any other chip or circuitry capable of performing the logic and control functions discussed herein. One type of microcontroller is MICROCHIP PIC12C509 (Microchip, Chandler, Ariz.), although other similar micro-controllers can be substituted by those skilled in the art.

The analog signal obtained as output from each sensor 51–53 is converted to a digital signal format via an internal analog-to-digital converter in the microprocessor 45. In alternate embodiments, the analog-to-digital conversion function can be performed external to the microprocessor 45 as shown (see External ADC 47). In addition to performing an analog-to-digital conversion function, the microprocessor 45 performs the functions of timing, identification, local data storage, communications protocol implementation and outputting digital signals to either transmission VCO circuit (see FIG. 4a) or a modulator 49 (see FIG. 4b).

FIGS. 4a and 4b illustrate alternate embodiments for transmitting data from the sensor platforms 100 to a field acquisition unit for receiving the transmitted data. The particular embodiment selected will depend on the sensor platform's 100 location and the surrounding environment.

Referring first to FIG. 4a, in a first embodiment, the sensor electronics 400 of the sensor platform is shown. In the first embodiment, data is transmitted from the sensor platforms 100 to a field acquisition unit (not shown) via an RF link, which is well known in the art. In accordance with a method for using an RF link, the transmission VCO circuit 49 is embodied as either an RF voltage or current controlled oscillator to drive the patterned transmit antenna 119 of FIG. 2. In this case, sensor data outputs of the microprocessor 45 modulate the transmission VCO circuit 49 using frequency shift keying FSK, which is well known in the art. The microprocessor driven transmission VCO circuit 49 then outputs one of two output frequencies dependent upon the modulation applied.

Referring now to FIG. 4b, the sensor electronics of FIG. 4b are similar in most respects to that of FIG. 4a with the following exceptions. In the second embodiment, data is transmitted from the sensor platform 100 to a field acquisition unit via absorption modulation, which is well known in the art. In accordance with this method, the modulator circuit 49 is embodied as a metal oxide semiconductor field effect transistor MOSFET or similar device having comparable switching characteristics. A data signal corresponding to a binary '1' from the microprocessor 45 causes the FET to turn on which causes extra or additional loading to be applied to the sensor platform's 100 pickup coil 46. This additional loading changes the loading characteristic of the sensor platform 100 relative to the external interrogation unit's power field generator. When the FET is turned on, this results in a small amplitude modulation of the voltage across the induction field generator coil of the interrogation unit. The resulting amplitude modulated (AM) signal can be processed at the interrogation unit to recover the transmitted data. In this case, no transmit antenna is required. Data is recovered simply by detecting the small amplitude modulation of the voltage at the interrogator unit (i.e., transmitter).

It should also be noted that the migration of the sensor electronics as described above, to a multi-chip module (MCM) assembly, chip on board assembly, buried LTCC resistors to further reduce the size and cost is possible.

One further adaptation contemplated by the present invention includes the use of a miniature off board oscillator 43, instead of the microcontroller's 45 on-board oscillator 43 shown, to further reduce power consumption.

An important technical advantage of the present invention is that the circuitry of sensor platform 100 may be powered by an induction field sent by an interrogation unit. Thus, sensor platform 100 does not need a battery or other local power source or power storage. Because no battery is needed, sensor platform 100 and associated circuitry may be placed in the structure to be monitored and thereafter require little to no maintenance of sensor platform 100.

Figure 5:
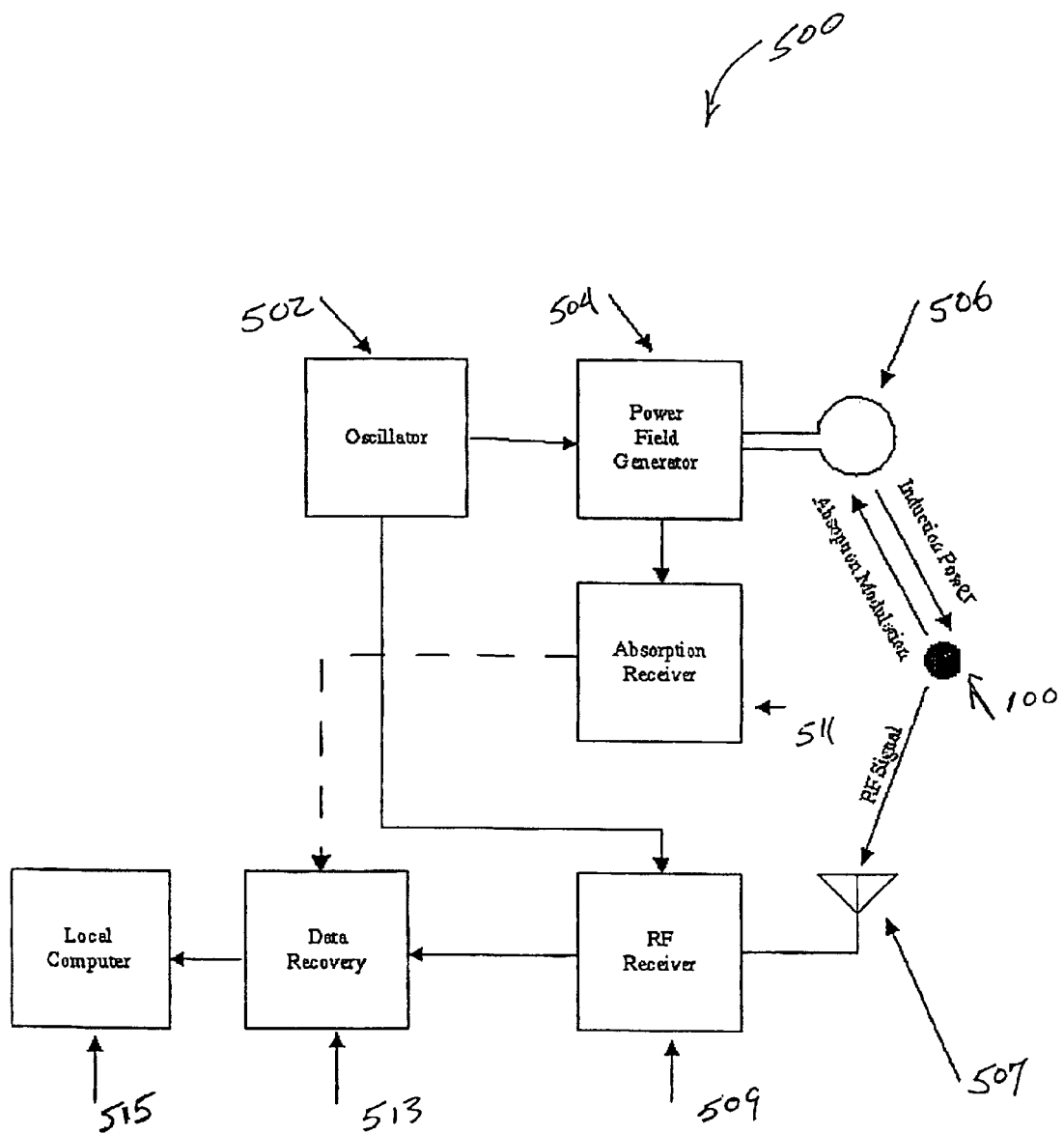
FIG. 5 is a block diagram of an interrogation unit used in accordance with the system of the present invention.

Turning now to FIG. 5, FIG. 5 is a functional block diagram of an interrogation unit 500 for powering the sensor platforms 100 and receiving data there-from. A primary function of the interrogation unit 500 is to generate a time varying magnetic field, i.e., an alternating current (AC) induction field to power the plurality of embedded sensor platforms 100 distributed throughout the medium to be monitored. This time varying magnetic field is generated by an AC current flowing in a one-turn coil. This coil on the interrogation unit 500 is mounted in such a way as to allow it to be placed directly over where the sensor is embedded. The AC current flowing in the one-turn coil is generated by an oscillator 502 which provides a stable operating frequency for the power field generator via crystal control. The output of the oscillator is amplified by a power field generator 504 which drives the one turn coil 506. The time varying magnetic field produced by the power field generator 504 induces an AC voltage in the power pickup coil 46 located inside the sensor platform 100. The induced AC voltage is rectified in the sensor platform 100 to produce a DC voltage as an input to the sensor platform's 100 voltage regulator (not shown). Internal to the sensor platform 100, a zener diode clamps the regulator's DC input voltage to a safe level. The output of the voltage regulator then provides power to the sensor platform's 100 remaining sensor electronics.

With continued reference to FIG. 5, there is shown a receiving antenna 507 for use when the sensor platforms 100 transmit their data to the interrogation unit 500 via an RF link. In this case, an RF receiver 509 is used to amplify and filter the RF signal. As shown, the oscillator 502 provides an input signal to the RF receiver 509 as part of the signal processing.

In the case where sensor platforms 100 transmit their data to the interrogation unit 500 via absorption modulation, the absorption receiver 511 is used. Irrespective of which receiving method is used, data recovery module 513 is used to provide final signal conditioning and interfacing to a local computer 515.

The following non-limiting example is illustrative of the multi-functional sensor system in accordance with the present disclosure.

EXAMPLE

Figure 6:
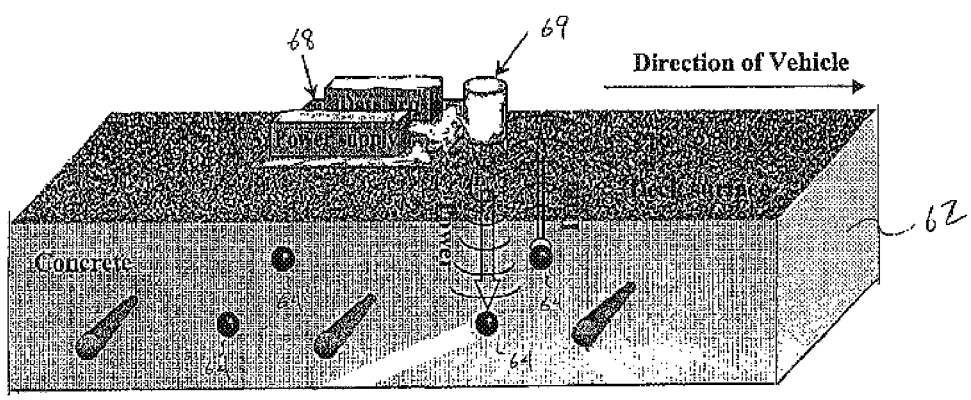
FIG. 6 is an illustration of an exemplary application of the present invention directed to bridge monitoring.

The operational concept of the multi-functional sensor system of the present invention is shown in FIG. 6 illustrating an exemplary application involving bridge monitoring. FIG. 6 illustrates a bridge structure 62 including a plurality of wireless embedded sensor platforms 64. For this particular application, the sensor platforms 64 are placed approximately every two meters throughout the structural elements of the bridge 62. The locations and densities of the sensor platforms 64 will depend on the particular structure being monitored.

As will be discussed below, information from the sensor platforms 64 will be transmitted during interrogation. The interrogation is performed with an interrogation unit 500 carried on a vehicle 68. The interrogation unit 500 records data from the sensor platforms 64 as the vehicle 68 passes in proximity to the sensor platforms 64. It should be understood that the interrogation unit 500 need not be carried on the vehicle 68, and may be hand held or permanently mounted near the structure to be monitored. With structures such as bridges, however, mounting the interrogation unit 500 on a vehicle allows for particularly convenient monitoring of environmental parameters.

The sensor platforms 64 are powered by near field induction (i.e., a power transmitter/reader) 69. As previously mentioned, the sensor platforms 64 are able to communicate with interrogation unit 500 through the use of radio frequency ("RF") waves or absorption modulation of the induction power field. With this approach, wireless, contactless reading of the sensor platforms 64 can be accomplished. Such communication provides an important technical advantage of the present invention, since reading of the sensor platforms 62 may be performed conveniently and quickly.

In operation, circuitry within the interrogation unit 500 generates an AC magnetic field, to power the sensor platforms 64, and receives data from the sensor platforms 62 for storage in a local computer in the interrogation unit 500.

Each of the plurality of sensor platforms 64 has a unique identification number that is recorded during installation. With individual ID numbers, the locations of particular sensors are maintained in a record, and data from those sensors can then be correlated with their position.

Figure 7:
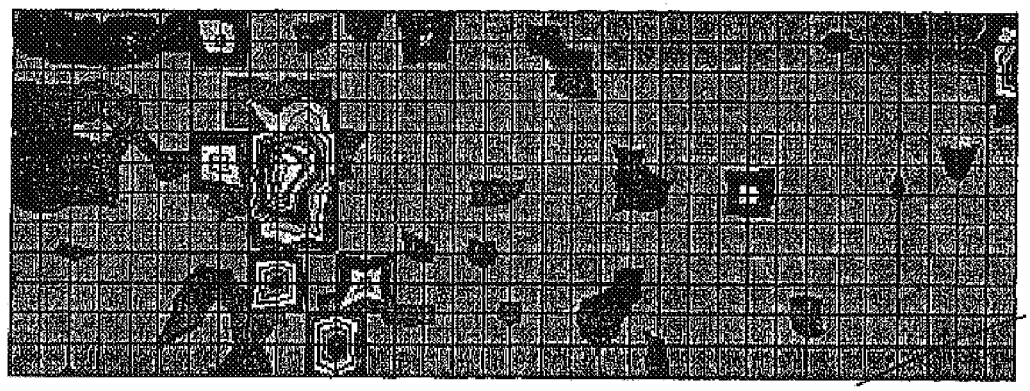
FIG. 7 is an illustration of a map generated as a product of using the system of the present invention for the illustrative bridge-modeling example of FIG. 6.

FIG. 7 is an exemplary illustration of a map that is generated as a product of using the system of the present invention in the illustrative bridge-modeling example of FIG. 6. As shown in FIG. 7, the gray-scale map indicates the variation in resistivity values in the bridge structure. In the present exemplary application, the resistivity values would be obtained by employing resistivity sensors in the sensor platforms 64 and recording data from the resistivity sensors. Such a map would localize areas of suspicion which would need to be monitored and/or repaired.

It will be understood that various modifications may be made to the embodiments disclosed herein. Therefore the above description should not be construed as limiting, but merely as exemplifications of preferred embodiments. For example, the functions described above and implemented as the best mode for operating the present invention are for illustration purposes only. Other arrangements and methods may be implemented by those skilled in the art without departing from the scope and spirit of this invention. Moreover, those skilled in the art will envision other modifications within the scope and spirit of the claims appended hereto.

APPENDIX A

Resistivity Sensor

The permeability of concrete refers to its ability to transport moisture, oxygen and chloride ions through concrete to the steel surface in the concrete. As is known through several studies, concrete with an electrical resistivity of 120,000 ohm-cm has a low permeability and low corrosivity whereas concrete with a resistivity of 10,000 ohm-cm or lower has high corrosivity. Therefore, electrical resistivity of concrete is a good indicator of its permeability to the potential corrosion agents. The range of resistivities expected is about 3 k to about 120 k cm-cm.

The resistivity sensor is based on a conventional four-probe technique; two probes to inject a current, and two probes to monitor the potential. In a typical arrangement, all four probes are equally spaced from each other with the two potential probes between the two current injection probes. The resistivity is computed using a modified form of Ohms Law from which the permeability is estimated. The applied current will be on the order of 10 microamperes ($\mu A$) at less than 1 V, and the total power requirement will be about 10 $\mu W.\backslash$ pH Sensor It is recommended to measure pH, in addition to chloride ion concentrations and temperature, to obtain a good estimate of corrosivity of the concrete environment. Commercial pH meters are unsuitable for this task because of reliability and size. The sensor under development is a calorimetric pH sensor, which uses an LED light source and a photo diode detector. It will measure pH changes in the 11 to 14 ranges and doesn't require calibration. The total power requirement for the sensor will be on the order of a few milliwatts. The wireless multi-functional sensor platform is being designed to accommodate this sensor.

Chloride Sensor

The chloride sensor includes at least two silver/silver chloride wires, one freely projecting into the concrete, and the other interfaced through a ceramic membrane saturated with potassium chloride (KCl). Each wire is about 1 cm long, and 2 to 5 mm in diameter. The chloride sensor will be calibrated after fabrication but will require no calibration at later times. It will measure the absolute level of chloride concentration in the concrete and requires very little power to operate.

Temperature Sensor

This sensor is a semiconductor-based sensor. Typically, due to the slow temperature transients expected inside concrete, the wireless multi-functional sensor platform should be in equilibrium with the adjacent concrete temperature. Therefore, the temperature sensor built into most microcontrollers can be used to sense the local concrete temperature.

Magnetometer Sensor

This sensor is a miniature sensor, which is sensitive to magnetic fields produced by currents in the $10^{-9}$ to $10^{+1}$ ampere range. It requires a few millewatts of power to operate. The magnetometer is used to sense electrical noise produced by the pitting corrosion activity and also can be used to measure stray currents or cathodic protection (CP) current in concrete structures.

Pitting corrosion is caused by the break down of the protective oxide film (passive film) on the metal surface. When the film is broken down (i.e., depassivated), the surface of the metal will corrode. The corrosion product will generate more of the (i.e., passive) metal oxide on the surface, preventing further corrosion. The corrosion reaction produces a current flow across the metal/concrete interface. During pitting, the depassivation-corrosion-repassivation process will repeat randomly, producing a temporal variation in the corrosion current. These fluctuations occur at low frequencies (<1 Hz), in the same range as electronic instrumentation noise or white noise. The noise associated with pitting corrosion, however, has several unique characteristics. Most forms of electronic and white noise will have a single temporal distribution. The electrochemical noise due to corrosion, on the other hand, has a bimodal distribution. The slope of the power spectrum plot is also unique for pitting corrosion, and can be used to indicate its presence.

The magnetic sensor envisioned by the applicants has a wide dynamic range. It can measure stray currents (~10 microamps; 100 nano Tesla): corrosion current (10 microamps, 100 nano Tesla); CP current (~1 milliamps; 10,000 nano Tesla) in the presence of a very large earth's magnetic field (50,000 nano Tesla).

It is noted that stray current electrolysis is a source of corrosion in concrete in industrial areas. Since rebars are buried in concrete, which is in contact with earth, the steel becomes an easy carrier of stray current. If the stray current has frequency components below a few Hz, it can quickly break down the oxide layer and cause pitting corrosion. Such a low frequency stray current can originate from light rail systems, high power industries, and heavy electrical engineering operations. Therefore, in urban and industrial environments where stray current is common, a concrete bridge may corrode even in the absence of chloride ions. The magnetometer sensor will identify the presence of stray current noise, characterize its frequency and amplitude, and even the points of stray injection and discharge.

What is claimed is:

1. A sensor system for monitoring of a medium, comprising:

an interrogation unit for generating an induction power field and for receiving responses; and a plurality of wireless embedded sensor platforms, each including a plurality of sensor types and powered by said induction field, said platforms are disposed throughout said medium, and wherein each of said plurality of sensor types generates a respective output representative of said sensor type, wherein each of said sensor platforms comprises:

a sensor housing having a cap portion and a base portion defining an interior volume, said plurality of sensors; and sensing electronics enclosed within said housing interior volume and operatively coupled to said plurality of sensors, said sensing electronics comprising:

a processor coupled to said plurality of sensors for monitoring outputs generated from said plurality of sensor types; and transmit circuitry coupled to said processor for transmitting said outputs representative of said sensor types.

2. The wireless sensor platform of claim 1, wherein said housing is made from a ceramic material.

3. The wireless sensor platform of claim 1, wherein said sensing electronics further includes means for being externally powered.

4. The sensor system of claim 1, wherein each sensor platform is made from a ceramic material.

5. The sensor system of claim 1, further comprising analog to digital conversion means for converting an analog output of said plurality of sensors to a digital output.

6. A sensor system for monitoring of a medium, comprising:

an interrogation unit for generating an induction power field and for receiving responses; and a plurality of wireless embedded sensor platforms, each including a plurality of sensor types and powered by said induction field, said platforms are disposed throughout said medium, and wherein each of said plurality of sensor types generates a respective output representative of said sensor type, further comprising a multi-layered substrate for mounting said sensing electronics.

7. The wireless sensor platform of claim 1 or 6, wherein said medium is selected from the group consisting of ground, asphalt, composites, plastics, concrete and cement.

8. The wireless sensor platform of claim 1 or 6, wherein said sensors sense a plurality of parameters selected from the group consisting of temperature, conductivity, pH, magnetism, noise, pressure, shock, strain, stress and vibration.

9. The sensor system of claim 6, wherein said multi-layered substrate is constructed of tape dielectric materials and screen printed thick-film conductor.

10. The wireless sensor platform of claim 1 or 6, wherein said sensors sense a plurality of parameters indicating structural, chemical and environmental conditions associated with the medium.

11. The sensor system of claim 6, wherein said multi-layered substrate is a low-temperature co-fired ceramic substrate.

12. The sensor system of claim 6, wherein one layer of said multi-layered substrate defines a patterned transmission antenna.

13. The sensor system of claim 6, wherein said plurality of wireless embedded sensor platform are individually addressable.

14. A method for providing monitoring of a medium, comprising the steps of:

providing a plurality of wireless embedded sensor platforms in said medium, wherein the medium is one of asphalt, concrete and cement, said sensor platforms having a housing defining an interior volume; and a plurality of sensors configured for inserting within said interior volume and for monitoring a plurality of parameters associated with said medium;

embedding the plurality of embedded wireless sensor platforms within the medium to be monitored;

generating a time varying magnetic field to said plurality of embedded wireless sensor platforms;

wirelessly receiving the time varying magnetic field at said plurality of embedded wireless sensor platforms;

powering said plurality of embedded wireless sensor platforms from the wirelessly received time varying magnetic field;

sensing a plurality of structural, chemical and environmental conditions of the monitored medium from said powered embedded wireless sensor platforms;

wirelessly transmitting said sensed plurality of structural, chemical and environmental conditions of the monitored environment to a receiving unit.

15. The method of claim 14, wherein the receiving unit is one of a mobile interrogation unit, a hand-held unit and a stationary unit.

16. The method of claim 14, wherein said receiving unit receives said sensed plurality of structural, chemical and environmental conditions while said receiving unit is in proximity with the monitored medium.

* * * * *

UNITED STATES PATENT AND TRADEMARK OFFICE
CERTIFICATE OF CORRECTION

PATENT NO. : 6,796,187 B2
DATED : September 28, 2004
INVENTOR(S) : Srinivasan et al.

It is certified that error appears in the above-identified patent and that said Letters Patent is hereby corrected as shown below:

Title page,
Item [75], Inventor, delete "Regaswamy" and insert therefore -- Rengaswamy --.

Signed and Sealed this

Eighth Day of February, 2005

JON W. DUDAS
*Director of the United States Patent and Trademark Office*